United States Patent [19]

Wondrazek et al.

[11] Patent Number: 5,041,121
[45] Date of Patent: Aug. 20, 1991

[54] SHOCK WAVE GENERATOR

[75] Inventors: Fritz Wondrazek, Pfaffenhofen; Frank Frank, Ebersberg; Stefan Hessel, Müchen; Stephan Thomas, Lübeck; Gisela Diepold, Germering, all of Fed. Rep. of Germany

[73] Assignee: Messerschmitt-Bölkow-Blohm GmbH, Fed. Rep. of Germany

[21] Appl. No.: 454,638

[22] Filed: Dec. 21, 1989

[30] Foreign Application Priority Data

Dec. 21, 1988 [DE] Fed. Rep. of Germany ....... 3842916

[51] Int. Cl.⁵ .............................................. A61B 17/22
[52] U.S. Cl. ....................................... 606/128; 606/15
[58] Field of Search ............. 606/2, 14, 15, 127, 606/128; 128/24 AA, 24 EL, 24.1

[56] References Cited

U.S. PATENT DOCUMENTS

| 3,982,541 | 9/1976 | L'Esperance | 606/14 |
| 4,211,229 | 7/1970 | Wurster | 606/14 |
| 4,784,132 | 11/1988 | Fox et al. | 606/15 |
| 4,878,725 | 11/1989 | Hessel et al. | 606/15 |
| 4,887,600 | 12/1989 | Watson et al. | 606/128 |
| 4,913,132 | 4/1990 | Gabriel | 606/14 |
| 4,932,954 | 6/1990 | Wondrazek et al. | 606/128 |

FOREIGN PATENT DOCUMENTS

| 3506249 | 8/1978 | Fed. Rep. of Germany | 606/128 |
| 3600713 | 7/1986 | Fed. Rep. of Germany | 606/128 |
| 3736953 | 5/1988 | Fed. Rep. of Germany | . |

OTHER PUBLICATIONS

Fair, Jr., "In Vitro Destruction of Urinary Calculi", Medical Instrumentation vol. 12, No. 2 (1978) pp. 100-104.

Primary Examiner—Lee S. Cohen
Assistant Examiner—John D. Zele
Attorney, Agent, or Firm—Evenson, Wands, Edwards, Lenahan & McKeown

[57] ABSTRACT

A shock wave generator for the fragmentation of concrements, having a light-pulse-transmiting light guide and a converter arranged at the distal light guide end and having an ionization surface which, when a light pulse impinges, initiates a shock wave in the surrounding fluid, as well as having a shock wave outlet zone. In order to increase its efficiency and durability, the generator is constructed such that the ionization surface extends obliquely sloped with respect to the beaming axis of the impinging light pulse and the shock wave outlet zone is arranged in the direct shock wave beaming area of the ionization surface, thereby permitting a largely unhindered, low-loss propagation for the shock wave to the application point.

12 Claims, 2 Drawing Sheets

SHOCK WAVE GENERATOR

BACKGROUND OF THE INVENTION

This invention relates to a shock wave generator, particularly for the fragmentation of concrements in hollow biological organs having a light-transmitting, particularly laser-light-transmitting light guide and a converter arranged at the distal light guide end which is equipped with a shock wave outlet zone and an ionization surface which, when a light pulse impinges on it, initiates a shock wave in the surrounding fluid.

Known shockwave generators of this type (e.g. DE-OS 37 36 953) are used as flexible application systems in intracorporal lithotripsy for producing laser-induced shock waves by means of the optical breakdown effect. These known shock wave generators have extremely small light guide and converter diameters of a magnitude of 1 to 2 mm. The converter is constructed as a hollow-cylindrical receiving housing which coaxially reaches around the light guide at the distal light guide end, and is open at one side. For reducing the light pulse density required for triggering the breakdown effect, the converter is equipped with a metallic ionization web which penetrates the shock wave emerging lumen of the converter in the area of the open housing end. The ionization surface of this ionization web faces the distal light guide end and extends vertically with respect to the beaming axis of the impinging light pulses, with a shock wave being generated in the surrounding fluid.

This shock wave, at least partially, first travels in the direct beaming area of the ionization surface inside the converter housing back to the light guide and to the interior housing walls, where it is reflected, before it can leave the converter by way of the outlet zone narrowed down by the ionization web and travel in the direction of the concrement to be fragmented. As a result of the energy loss of the shock wave on the way between the ionization surface and the converter outlet, shock wave generators of this type have a limited efficiency and durability, mainly in the area of the distal light guide end situated in the main direction of the backwards-travelling shock wave.

It is an object of the invention to construct an optoacoustic shock wave generator of the initially mentioned type in such a manner that, by means of an improved guiding of the shock wave in the converter, the usable electric-wave energy and the stability of the shock wave generator are clearly increased.

According to the invention, this object is achieved by means of the shock wave generator constructed such that the ionization surface extends obliquely sloped with respect to the beaming axis of the impinging light pulse, and the shock wave outlet zone of the converter is arranged in the direct shock wave beaming area of the ionization surface.

In the case of the shock wave generator according to the invention, it is ensured, as a result of the special assignment of the ionization surface with respect to the beaming axis of the light guide, on the one hand, and of the shock wave outlet zone, on the other hand, that the shock wave load of the generator, mainly in the light-guide-side converter areas which are particularly sensitive in this respect, is reduced considerably and the shock wave propagates largely unhindered from the ionization surface, by way of the converter outlet, to the application point. As a result, the shock wave energy which can be used at the application point is increased considerably in relation to the beamed-in light pulse energy, and the mechanical stability of the shock wave generator is clearly improved. The shock wave generator according to the invention is therefore excellently suitable for the direct fragmentation of concrements by shock waves at points which are difficult to reach, such as urinary or renal calculi in the human body.

In a further advantageous development of the invention, the ionization surface is preferably sloped at an angle of 20° to 60° with respect to the beaming axis of the light pulse, whereby, without any focussing of the light pulse, a sufficiently high luminance can be achieved at the ionization surface with a simultaneous particularly advantageous mutual assignment of the distal light guide end, the ionization surface and the outlet zone of the converter. So that the renewal of the ionization surface, at which the luminance of the light pulses required for initiating the breakdown effect must be in the magnitude of $10^9$ W/cm$^2$, takes place without any problems, the ionization surface is preferably constructed at an exchangeable carrier element of the converter.

In order to effectively prevent in a simple manner a penetrating of floating particles, such as fragments of the concrement to be broken up, into the beaming path of the light pulses between the distal guide end and the ionization surface, a rinsing duct is expediently provided which in addition to the light guide, is connected to the converter and is used for supplying a rinsing fluid which flows around the distal light guide end and flows off toward the ionization surface; and in view of a particularly advantageous rinsing of the interior of the converter, the rinsing duct, preferably contains several rinsing-fluid outlet openings which are uniformly distributed in circumferential direction in the area of the distal guide end, in which case, a water-containing fluid is expediently used as the rinsing fluid which exhibits the desired optical characteristics concerning a low-threshold triggering of the breakdown effect as well as permits a transmission of the shock wave aimed directly at the application point which is as low in losses as possible.

For manufacturing reasons, the ionization surface is preferably constructed to be flat; however, it may optionally, for example, in view of a uniform luminance distribution, in the case of a generally slightly divergent inherent beaming characteristic of the light guide, also be bent.

According to a particularly preferred aspect of the invention, the converter consists of a hollow-cylindrical receiving housing which contains a carrier element which, in the manner of a finger, projects beyond the open housing end and is provided with the ionization surface, in which case, an outlet zone is obtained laterally of the housing axis which is no longer restricted by the inside diameter of the housing and through which the shock wave created at the ionization surface can pass almost completely on its direct path in the direction toward the application point. In this case, the beaming axis of the light guide in view of a simple fastening of the light guide, expediently extends in the direction of the central axis of the housing, in which case, the light guide can not only be fastened coaxially preferably—eccentrically with respect to the central axis of the housing in the receiving housing, in which case, the eccentric fastening results in a flatter slope of the ionization surface with respect to the central axis of the housing and therefore in an enlargement of the outlet zone and a more forwardly directed shock wave propagation. For an arrangement of the ionization surface which is directed further away from the open housing end toward the front, it is recommended to fasten the light guide obliquely with respect to the central axis of the housing in the receiving housing.

According to another variant of the invention which is particularly simple with respect to manufacturing, in connection with a converter which is again constructed as a hollow-cylindrical receiving housing, a circumferential beaming characteristic at the distal light guide end which is achieved by an oblique, proximal-side coupling-in of the light pulse is utilized in such a manner that the light pulse, as an annular cone which is coaxial with respect to the central axis of the housing, is aimed obliquely at the part of the interior wall of the cylinder which is adjacent to the open housing end and which forms the ionization surface. By means of the distribution of the light pulse which is uniform in circumferential direction and extends over the annular zone extending around the housing opening, the stability of the converter is further increased and it is ensured at the same time that the forming shock wave can propagate on a direct path by way of the free housing opening unhindered toward the front to the application point, thus, for example, to the calculus to be destroyed.

The invention will now be explained in detail by means of embodiments shown in the figures.

In a very schematical enlarged representation,

Figure 1:
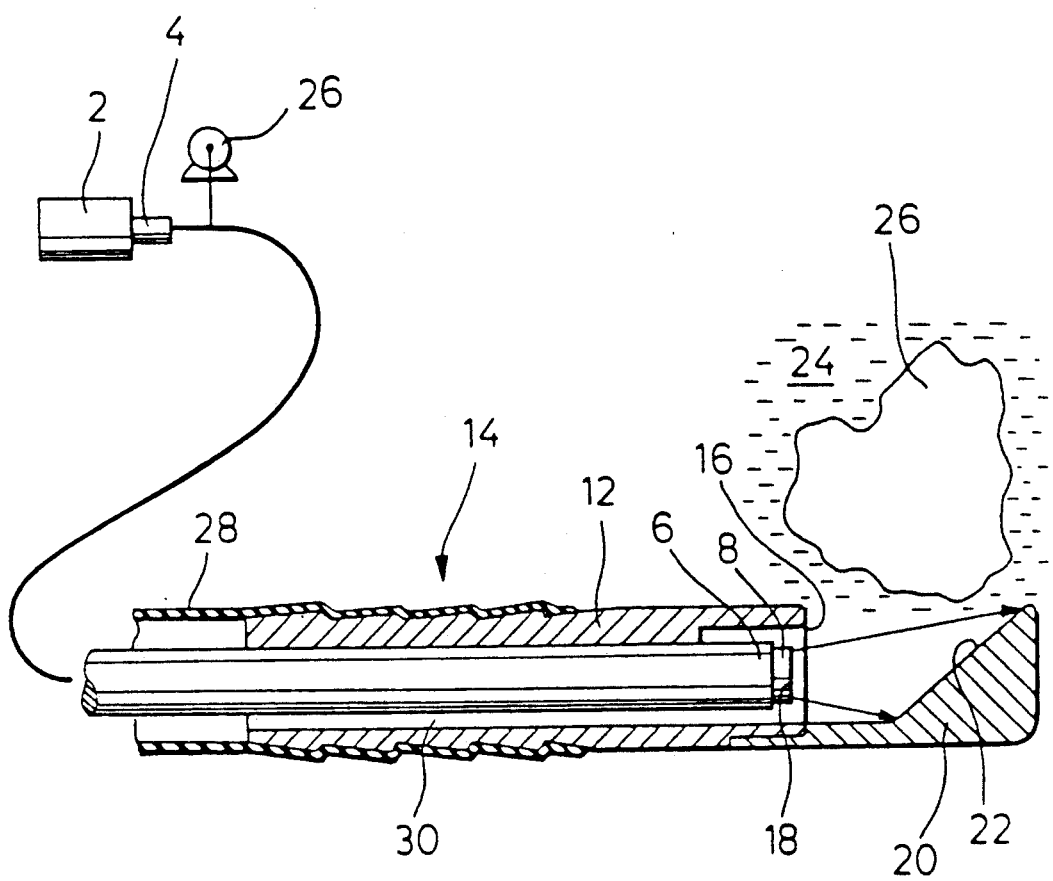
FIG. 1 is a partially sectional view of a first embodiment of a shock wave generator.

The embodiment shown in FIG. 1 has a laser 2 which is suitable for generating light pulses with a pulse duration of approximately 10 ns and an energy of up to 50 mJ which, by way of a coupling-in lens system 4, are coupled into the proximal end face of a flexible optical fiber 8 sheathed by a fiber covering 6. This optical fiber is fastened in the distal-side end area in the metallic, hollow-cylindrical receiving housing 12 of a converter which, as a whole, has the reference number 14, coaxially with respect to the central axis of the housing so that the beamed-in laser light pulses, at the distal light guide end face 18 situated close to the open housing end 16, are beamed out as a cone of light which is coaxial with respect to the housing axis and has half a vertical and opposite angle of approximately 10°, as shown by the edge beams entered in FIG. 1.

At an exchangeable, also metallic carrier element 20 of the receiving housing 12 which extends in the manner of a finger toward the front beyond the housing opening 16, a flat ionization surface 22 is formed which is sloped at approximately 40° obliquely with respect to the beaming axis of the light pulses and on which the light pulses impinge with a luminance of approximately $10^9$ W/cm$^2$ and generate a shock wave in the surrounding fluid 24 which, in lateral direction propagates unhindered by way of the outlet zone kept free between the housing end 16 and the ionization surface 22, on a direct path, to the concrement 26 situated in front of the outlet zone.

The fluid 24, in which the breakdown effect generating the shock wave is produced by means of the laser pulses at the ionization surface 22, (which can be elliptic although not shown in FIG. 1) should have the desired optical characteristics with respect to the breakdown effect and should also ensure a transmission of the forming shock wave which has as few losses as possible and, as a rule, consists of a water-containing biologically tolerable liquid which is supplied to the converter 14 by a rinsing fluid pump 26 in a fluid hose 28 which is coaxial with respect to the light guide 6, 8 and, by way of several rinsing slots 30 of the receiving housing 12 which are uniformly distributed in circumferential direction, in the area of the distal light guide end, emerges into the housing lumen and flows off in the direction of the ionization surface 22 by way of the shock wave outlet zone. As a result of the mutual spatial assignment of the ionization surface 22, the light guide beaming axis and the shock wave outlet zone of the converter 14, the laser pulse energy, with a very high efficiency, specifically with an efficiency that is increased threefold with respect to comparable conventional converters, is converted to usable shock wave energy. At the same time, the converter 14, because of its small dimensions of, for example, an overall length of 10 mm and an outside diameter of 2 mm, can be applied in the most narrow space directly to the concrement 26 to be destroyed.

Figure 2:
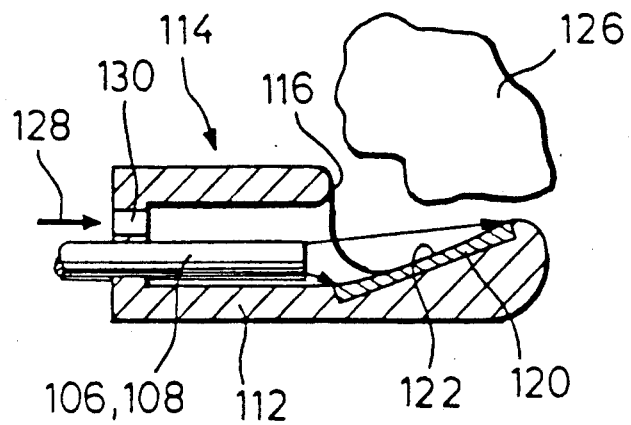
FIG. 2 is a view of the shock wave generator according to FIG. 1 in the area of the converter housing with a modified light guide fastening.

According to FIG. 2, where the elements corresponding to the first embodiment are marked by a reference number that is increased by 100, the light guide 106, 108 is eccentrically fastened in the receiving housing 112 and the elliptic ionization surface 122 which is developed at the exchangeable carrier element 120 is correspondingly also arranged eccentrically with respect to the central axis of the housing, whereby the shock wave outlet zone of the converter 114 is enlarged and the direct shock wave beaming area of the ionization surface 122 is directed more toward the front. While the eccentric light guide arrangement is taken into account, the rinsing-fluid ducts 130 are not distributed uniformly in circumferential direction but, for space reasons, extend on one side above the light guide 106, 108 in the converter housing 112. Apart from that, the construction and the operating method of the converter 114 is the same as in the embodiment according to FIG. 1.

Figure 3:
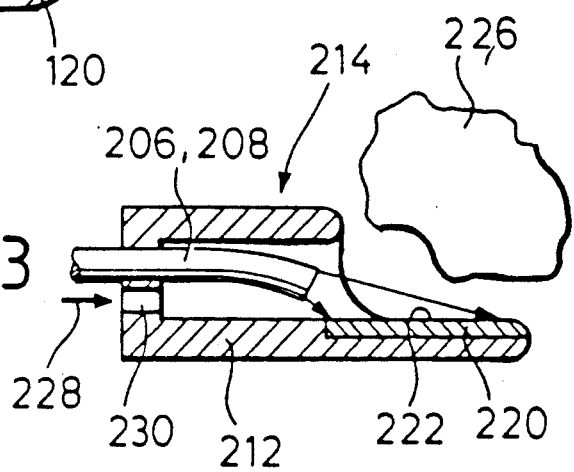
FIG. 3 is a representation corresponding to FIG. 2 as another modification.

In a representation corresponding to FIG. 2 and with reference numbers increased by 200, FIG. 3 shows a further modified embodiment in which the light guide 206, 208 is contained in the converter housing 212 not only in an eccentric but also in a bent manner, whereby the angle of slope of the ionization surface 222, with respect to the central axis of the housing, while an oblique adjustment with respect to the beaming axis of the light pulse is maintained, can be changed in such a manner that, in comparison to FIG. 2, another enlargement is obtained of the converter outlet zone situated in the direct beaming area of the ionization surface 222 as well as a shock wave propagation which is directed even more toward the front. The arrangement of the rinsing ducts 230, just like the remaining construction and method of operation of the converter 214 is the same as according to FIG. 2.

Figure 4:
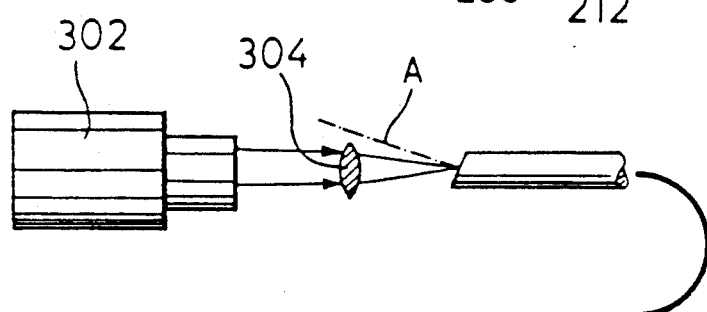
FIG. 4 is a partially sectional view of a shock wave generator according to a second embodiment.
Figure 4:
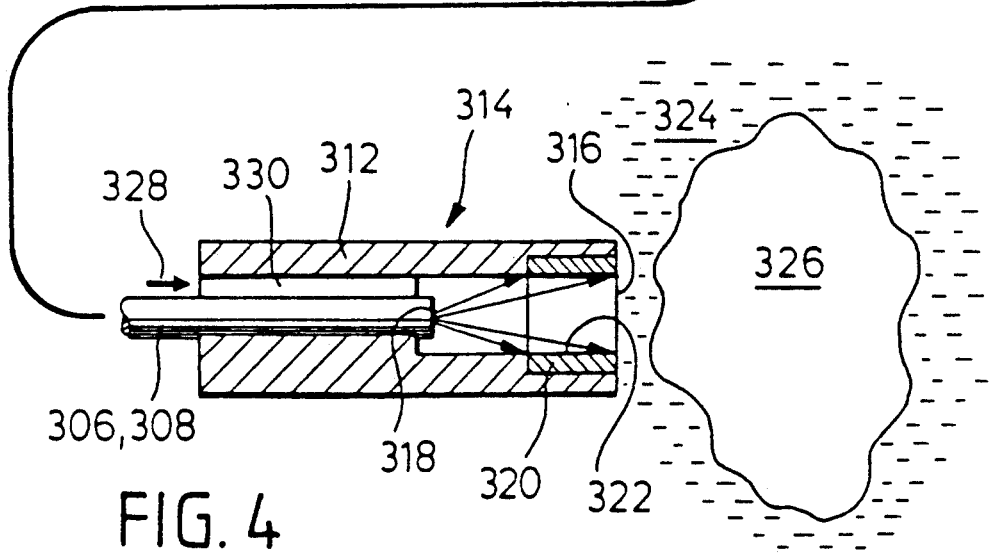

In the shock wave generator according to FIG. 4, where the components corresponding to the first embodiment are provided with reference numbers which are increased by 300, the light guide 306, 308 is again contained in a hollow-cylindrical converter housing 312 coaxially with respect to the housing axis, which is provided with rinsing slots 330 which are uniformly distributed in circumferential direction. However, in contrast to the previously described embodiments, in this case, the part of the cylindrical interior wall of the housing which is adjacent to the free housing opening 316 is constructed as an ionization surface 322 at an annular-bush-shaped exchangeable insert element 320. The oblique assignment of the ionization surface 322 with respect to the beaming direction of the light pulses is achieved in that the light pulses, by way of the coupling-in lens system 304, at an acute angle with respect to the normal surface line A, at the proximal light guide end, are coupled into the light guide inlet surface, so that they are emitted at the distal light guide end face 318 with a circumferential beaming characteristic in the form of an annular cone which is coaxial with respect to the central axis of the housing and is directed to the ionization surface 322, as indicated in FIG. 4 by means of the annular-cone edge beams. Also in this embodiment, the ionization surface 322, with respect to the beaming direction of the light pulses, is therefore sloped obliquely in the direction of the shock wave outlet zone formed by the free housing opening 316 and situated in the direct shock wave bearing area of the ionization surface 322. As a result of the annularly emerging intensive laser light, a plasma is produced at the ionization surface 322 around the housing opening 316 and a shock wave is formed which propagates toward the front unhindered to the concrement 326. Apart from that, the construction and method of operation corresponds to that of the first embodiment.

We claim:

1. An acoustic shock wave generator for the fragmentation of concrements in hollow biological organs, comprising a source of laser light pulses, a laser-light-transmitting light guide connected to the source and a converter arranged at a distal light guide end, said converter including an ionization surface means for converting an impinging laser light pulse into an acoustic shock wave in the surrounding fluid and a shock wave outlet zone, wherein the ionization surface means extends obliquely sloped with respect to a beaming axis of an impinging laser light pulse, and the shock wave outlet zone of the converter is arranged in a direct shock wave beaming area of the ionization surface means.

2. A shock wave generator according to claim 1, wherein the ionization surface means is sloped at an angle of 20° to 60° with respect to the beaming axis of the laser light pulse.

3. A shock wave generator according to claim 1, further comprising a carrier element which is exchangeably fastened to the converter, said ionization surface means being situated at said carrier element.

4. A shock wave generator according to claim 1, further comprising a rinsing duct which is connected to the converter in addition to the light guide, for supplying a rinsing fluid which flows around the distal light guide end and flows off in the direction toward the ionization surface means.

5. A shock wave generator according to claim 4, wherein the rinsing duct contains several rinsing fluid outlet openings which, uniformly distributed in circumferential direction in the area of the distal light guide end, lead into the interior of the converter.

6. A shock wave generator according to claim 1, wherein the ionization surface means is constructed to be flat.

7. A shock wave generator according to claim 1, wherein the converter further comprising a hollow-cylindrical receiving housing which surrounds the light guide and is freely opened at one end and has a carrier element which projects in the manner of a finger beyond the open housing end and is provided with said ionization surface means.

8. A shock wave generator according to claim 7, wherein the beaming axis of the laser light pulse extends in the direction of a central axis of the housing.

9. A shock wave generator according to claim 8, wherein the light guide is fastened in the receiving housing coaxially to the central axis of the housing.

10. A shock wave generator according to claim 7, wherein the light guide is fastened in the receiving housing eccentrically with respect to a central axis of the housing.

11. A shock wave generator according to claim 7, wherein at least a portion of the light guide is fastened in the receiving housing obliquely with respect to a central axis of the housing.

12. A shock wave generator according to claim 1, wherein the converter is constructed as a hollow-cylindrical receiving housing which houses the light guide and has a freely opened cylinder end that defines the shock wave emerging zone, the section of the interior wall of the receiving housing situated at the open cylinder end being the annular ionization surface means, and the laser light pulses at the proximal light guide end being obliquely coupled in such manner that they emerge at the distal light guide end with a circumferential beaming characteristic in the form of an annular cone directed at the ionization surface means.

* * * * *